(12) United States Patent
Schüller et al.

(10) Patent No.: US 8,099,166 B2
(45) Date of Patent: Jan. 17, 2012

(54) IMPLANTABLE MEDICAL DEVICE WITH LEAD FAILURE DETECTION

(75) Inventors: Hans Schüller, Lund (SE); Anders Lindgren, Täby (SE)

(73) Assignee: St. Jude Medical AB, Jarfalla (SE)

( * ) Notice: Subject to any disclaimer, the term of this patent is extended or adjusted under 35 U.S.C. 154(b) by 216 days.

(21) Appl. No.: 12/439,036

(22) PCT Filed: Aug. 28, 2006

(86) PCT No.: PCT/SE2006/000984
§ 371 (c)(1),
(2), (4) Date: Feb. 26, 2009

(87) PCT Pub. No.: WO2008/026969
PCT Pub. Date: Mar. 6, 2008

(65) Prior Publication Data
US 2010/0010558 A1    Jan. 14, 2010

(51) Int. Cl.
*A61N 1/37* (2006.01)
(52) U.S. Cl. .......................................... 607/27
(58) Field of Classification Search .......... 607/27–30
See application file for complete search history.

(56) References Cited

U.S. PATENT DOCUMENTS

| | | |
|---|---|---|
| 5,558,098 A | 9/1996 | Fain |
| 5,776,168 A | 7/1998 | Gunderson |
| 5,792,205 A | 8/1998 | Alt et al. |
| 6,236,882 B1 | 5/2001 | Lee et al. |
| 2003/0204215 A1 | 10/2003 | Gunderson et al. |
| 2004/0162593 A1 | 8/2004 | Jorgenson et al. |

OTHER PUBLICATIONS

Automatic Identification of Implantable Cardioverter-Defibrillator Lead Problems Using Intracardiac Electrograms, Gunderson et al., Computers in Cardiology, vol. 29 (2002) pp. 121-124.

*Primary Examiner* — Scott Getzow
(74) *Attorney, Agent, or Firm* — Schiff Hardin LLP

(57) ABSTRACT

An implantable heart stimulating device has an ECG sensing unit to receive heart potential signals from sensing electrodes at an electrode lead arranged in connection with a patient's heart. The ECG sensing unit is provided with a programmable make-break threshold. The device further has a timer adapted to generate a make-break detection period, and a counter. The counter is adapted to count the number of times that the amplitude of the heart potential signal exceeds the programmable make-break threshold during the make-break detection period. When the number of times is higher than a predetermined value, the ECG obtained during the make-break detection period is stored in an ECG storage unit.

10 Claims, 2 Drawing Sheets

IMPLANTABLE MEDICAL DEVICE WITH LEAD FAILURE DETECTION

BACKGROUND OF THE INVENTION

1. Field of the Invention

The present invention relates to an implantable heart stimulating device such as a pacemaker, defibrillator or cardioverter, having electrode leads having stimulation surfaces adapted to apply stimulation energy to heart tissue.

2. Description of the Prior Art

An early indication of lead insulation defects, broken/damaged lead conductors and loose set screws/improper lead connection may be provided by the intermittent occurrence of so-called make-break signals, which then may remain unrecognized for a longer period of time. Even extensive follow-up evaluation of a sporadic symptomatic patient often fails to disclose indications of an imminent lead or lead connector failure, since the make-break signals might only be prevailing in a certain, specific body position.

Make-break signals may arise when:

- The lead conductors make intermittent contact with each other due to an inner lead insulation defect/damage.
- The outer conductor makes intermittent contact with the pulse generator housing due to an outer insulation defect/damage (caused by the lead insulation being rubbed off against the pulse generator housing).
- The outer conductor makes intermittent contact with the outer conductor of another lead due to the fact that the leads have crossed each others in the pulse/ICD pocket and rubbed off each others insulations.
- The two ends of a broken lead conductor meet intermittently.
- A loose set screw.
- A lead connector pin not fully inserted into the pulse generator connector.
- The electrode(s) or outer insulation defects touches the electrodes of another lead inside the heart.

Make-break signals may cause:

- Inhibition/triggering of pacemaker stimulation.
- Noise mode reversion with risk for T-wave stimulation.
- Triggering of inappropriate ICD therapy.

It is realistic to assume, that lead insulation/conductor damages as well as connector problems in pacemaker/ICD systems will continue to occur to some extent also in the future. According to clinical experience incipient lead and/or connector failures are often difficult to disclose at an early stage.

Thus, the development of life threatening conditions in some patients may remain unrecognized for substantial periods of time despite normal follow-up intervals. However, early disclosure of lead and connection failures is of outmost importance for patient safety and would benefit from new, preferably automatic, diagnostic approaches.

U.S. Pat. No. 5,558,098 relates to a method and apparatus for detecting lead sensing artefacts in cardiac electrograms, the sensing artefacts are caused by lead conductor fracture, lead insulation failure or connector port fluid penetration. The system includes at least two pairs of sensing electrodes which provide two distinct electrogram signals to the sensing and analysis circuitry of a pulse generator. Each signal is analyzed for heart rate. The rates are compared and if the rates detected are significantly different therapy is not delivered to the patient. In an alternative embodiment, the two signals are compared by performing a correlation analysis.

In this known device a comparison between two distinct electrogram signals from at least two pairs of sensing electrodes is performed in order to obtain an indication of e.g. a lead conductor fracture.

A drawback of this known device is that extra hardware is required, e.g. in the form of extra sensing electrodes and means for connecting the electrodes to the measurement means, in order to perform the measurement.

SUMMARY OF THE INVENTION

An object of the present invention is to provide an implantable heart stimulating device, provided with a detector to detect e.g. lead connector fractures or damages, that is easily implemented into a heart stimulating device and that does not require extra hardware.

According to the present invention an implantable heart stimulating device has an ECG sensing system that receives heart potential signals from sensing electrodes at an electrode lead arranged in connection with a patient's heart. The ECG sensing system has a programmable make-break threshold, and the device further has a tuner that defines a make-break detection period, and a counter that counts the number of times that the amplitude of the heart potential signal exceeds the programmable make-break threshold during the make-break detection period. When the number of times is higher than a predetermined value, the ECG obtained during the make-break detection period is stored in an ECG storage means.

The stored ECG signal may then be further analyzed in order to determine if the indication of a lead defect is valid. This occasional occurrence of make-break signals could be identified, for example, at routine follow-ups by retrieving the internal device memory.

Thus, by initiating storing of electrocardiograms (including sensed event registration) in the presence of intermittent male-break signals early identification of impending lead/connection failures can be made, well before progress into life-threatening conditions.

No extra hardware is required to implement the invention since all modern pacemakers and ICD's are able to store electrocardiograms intended to reveal a variety of preset rhythm anomalies, and includes programming capabilities to implement the timing and counting components.

Generally, the present invention provides a new triggering event for storing ECG-segments to be further analysed.

DESCRIPTION OF THE PREFERRED EMBODIMENTS

Figure 1:
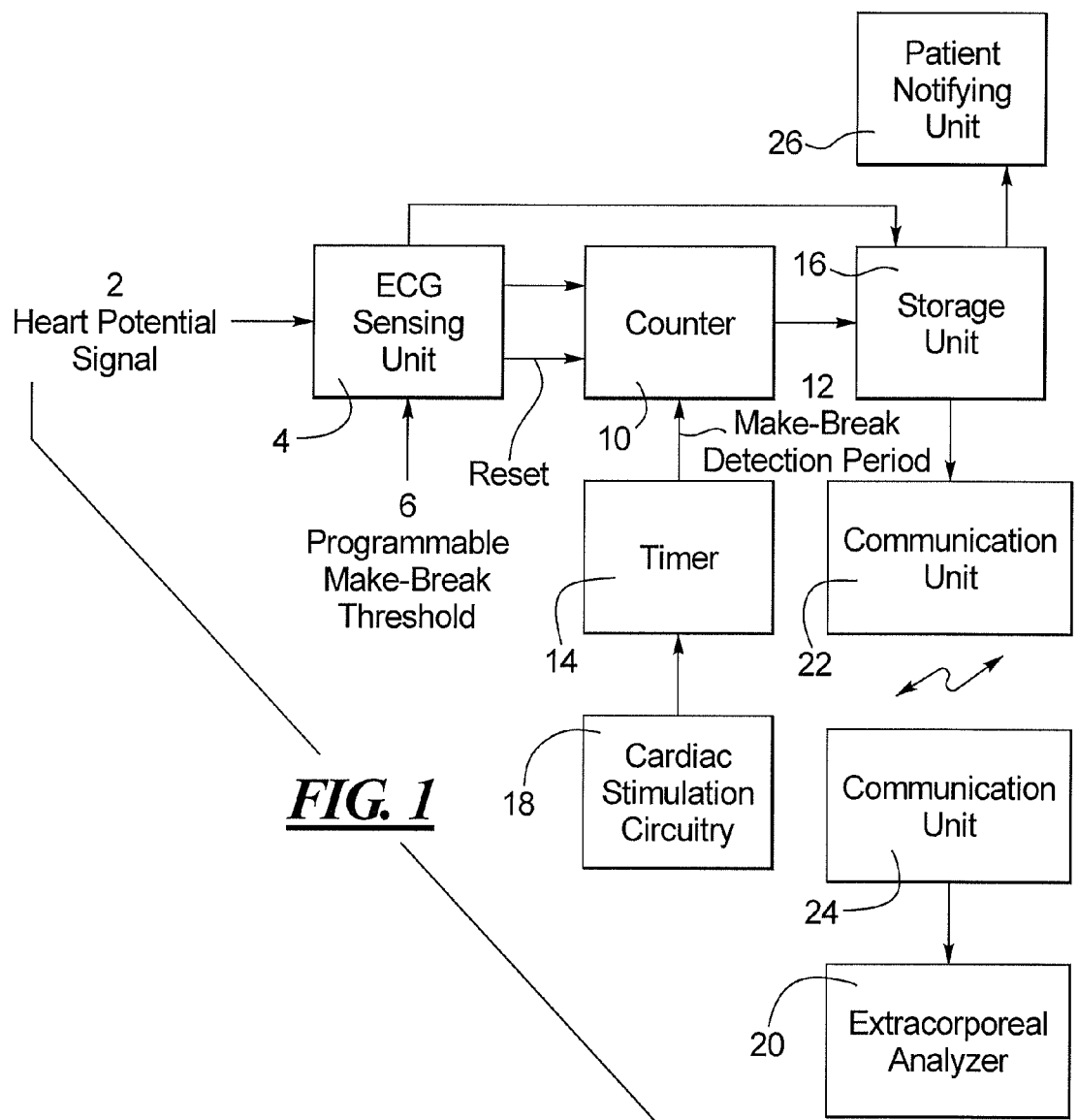
FIG. 1 shows a schematic block diagram illustrating the heart stimulating device according to the present invention.

FIG. 1 shows a schematic block diagram illustrating the heart stimulating device according to the present invention.

FIG. 1 shown an implantable heart stimulating device having an ECG sensing unit 4 adapted to receive heart potential signals 2 from sensing electrodes (not shown) arranged in connection with a patient's heart. The ECG sensing unit 4 includes amplifier means, filtering means and other signal processing means, which all are commonly used in implantable heart stimulating devices and therefore need not be further discussed herein. The ECG sensing unit 4 is provided with a programmable make-break threshold. The stimulating device further has a timer 14 adapted to generate a make-break detection period 12, and a counter 10. The counter 10 is adapted to count the number of times that the amplitude, preferably the absolute amplitude, of the heart potential signal exceeds the programmable make-break threshold during the make-break detection period. When the number of times is higher than a predetermined value, the counter 10 enables storage of the ECG obtained during the make-break detection period in an ECG storage unit 16. Preferably, the predetermined value is 3, 4 or 5, but any higher value may also be used.

The counter 10 and the timer 14 are preferably implemented in software. According to another preferred embodiment the make-break detection period is initiated when, and in parallel to, a refractory period, used in connection with normal heart stimulation procedures, is initiated by cardiac stimulating circuitry 18. The make-break detection period may also be initiated by a premature ventricular contraction (PVC) or by another predefined intrinsic or stimulated heart event.

According to another preferred embodiment the make-break detection period has a programmable length being a programmable percentage, between 20-100%, of the length of the escape interval used in connection with normal heart stimulation procedures by the cardiac stimulating circuitry 18. If the detection period has a length of 100% of the escape interval the make-break signal detection is constantly activated, i.e. it enables detection of make-break signals during the entire heart cycle.

The counter 10 is reset after each heart cycle by the ECG sensing unit 4.

The stored ECG may be analyzed, either by analysis circuitry or software (not shown) integrated in the medical device or in an external analyzer 20 in an external programming device, i.e., a "programmer", in order to detect defects or damages of the electrode leads and/or electrode connections. Preferably, the programmer, through a communication session between a communication unit 22 in the implantable device and a communication unit 24 in the programmer, directly alerts the physician that a lead failure has been indicated.

In addition, the implantable device may be provided with a patient notifying unit 26 adapted to notify the patient in case of detected anomalies. The notifying may be achieved by sound or by a generated vibration.

Figure 2:
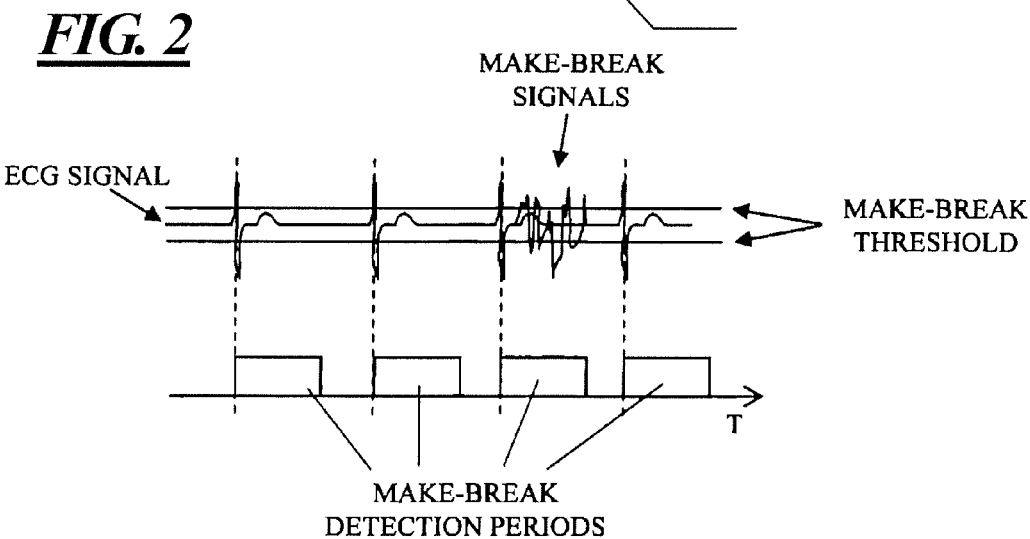
FIG. 2 shows the present invention implemented on an ECG signal.

FIG. 2 shows the present invention implemented based on an ECG signal. In FIG. 2 four heart cycles are shown by schematically illustrated QRS-complexes, either intrinsically initiated or stimulated by the heart stimulating device. In this case make-break detection periods are initiated when the QRS-complexes occur.

In FIG. 2, make-break signals occur in the third heart cycle and in this specific example the absolute ECG signal exceed the make-break threshold at least nine times during the make-break detection period and if the predetermined value is e.g. four, the ECG signal during the third heart cycle will be stored.

Figure 3:
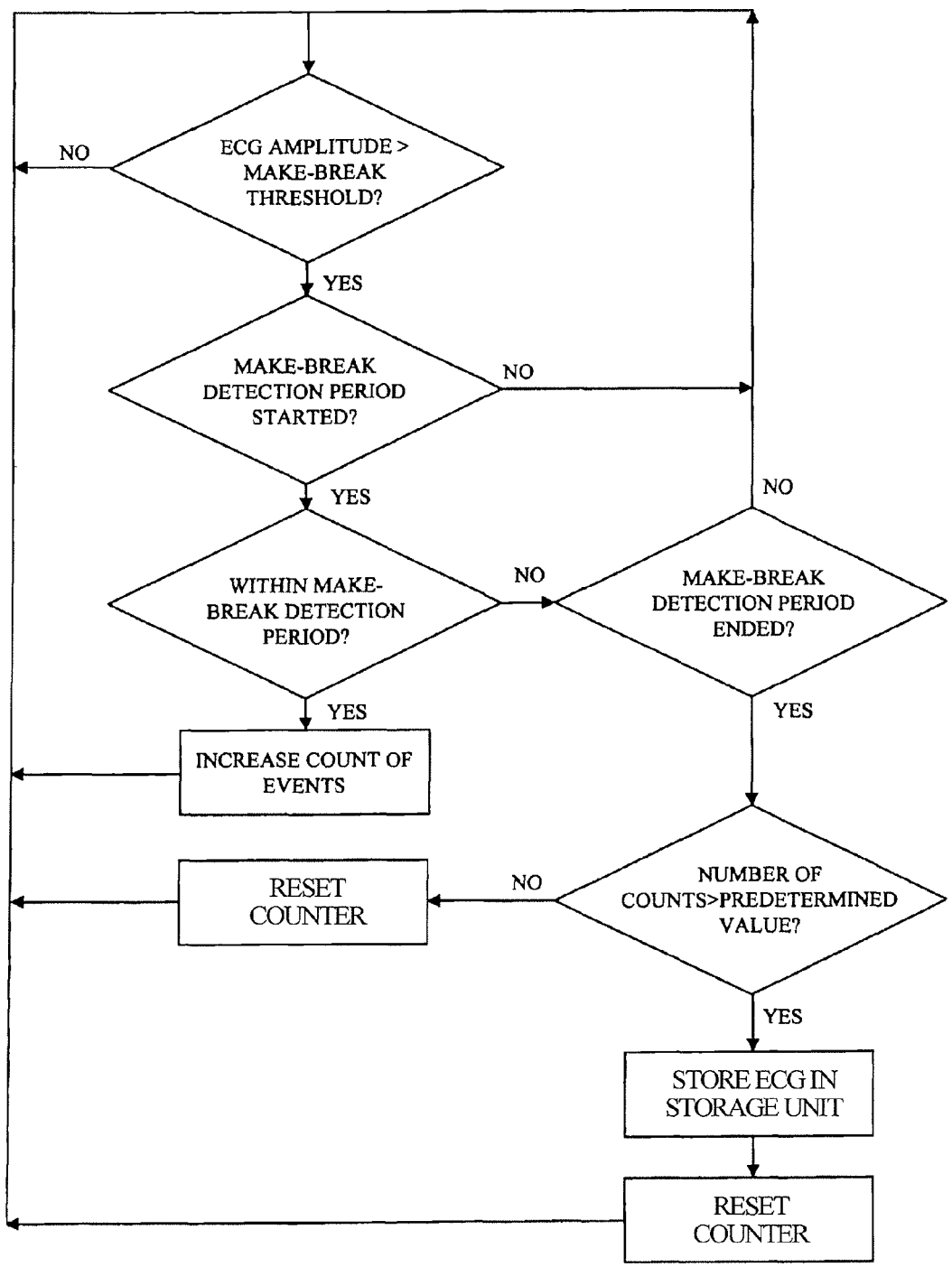
FIG. 3 is a flow diagram illustrating the present invention.

FIG. 3 is a flow diagram schematically illustrating the present invention.

In the first box of the flow diagram the (absolute) ECG amplitude of the ECG-signal is compared to the programmable make-break threshold and if the amplitude is greater than the threshold it is determined, in the second box, whether the ECG-signal is measured within the make-break detection period. If within the period the count performed by the counter 10 is increased. If not within the detection period and the detection period has ended it is checked if the number of count is greater than a predetermined value. If it is not greater, the counter 10 is reset and the procedure returns to the first box for ECG amplitude measurement. If the number of counts during the detection period is greater than the predetermined value the ECG signal during the present heart cycle is stored in the storage unit 16, for further analysis, and the counter 10 is reset.

If it is determined as a result of the analysis that the electrode lead is damaged the physician has to decide if the electrode lead should be replaced or if any other procedures should be undertaken, e.g. reprogramming of the pacemaker.

The present invention may naturally also be used to store ECG-signals having the erratic nature of a make-break signal, but not caused by e.g. an electrode damage, but instead caused by any heart event, e.g. R on T phenomenon or retrograde P-waves, for later analysis.

Although modifications and changes may be suggested by those skilled in the art, it is the intention of the inventors to embody within the patent warranted hereon all changes and modifications as reasonably and properly come within the scope of their contribution to the art.

The invention claimed is:

1. An implantable heart stimulating device comprising:
an electrode lead configured for in vivo implantation in a patient, said electrode lead carrying at least one sensing electrode configured to interact with the heart of the patient, as a part of a complete current path, when the electrode lead is implanted in the patient;
an ECG sensing unit that receives cardiac potential signals from said electrode;
said ECG sensing unit being provided with a non-temporal make-break threshold indicative of a magnitude of said cardiac potential signal associated with an absence of successive making and breaking of said current path, said ECG sensing unit being configured to emit an output signal at a first output of said ECG sensing unit whenever said cardiac potential signal exceeds said threshold;
a timer that generates a make-break detection period;
a counter connected to said first output of said ECG sensing unit that generates a count representing a number of times that said cardiac potential signal exceeds said make-break threshold; and
a storage unit connected to said counter and to a second output of said ECG sensing unit, said counter being configured to cause transfer of the cardiac potential signal obtained during said make-break detection period from said second output of said ECG sensing unit to said storage unit if said count in said make-break detection period exceeds a predetermined value.

2. An implantable heart stimulating device as claimed in claim 1 comprising heart stimulating circuitry that operates with a refractory period, and wherein said timer is connected to said heart stimulating circuitry and is configured to start said make-break detection period coinciding with a start of said refractory period.

3. An implantable heart stimulating device as claimed in claim 1 comprising heart stimulating circuitry that operates with a refractory period, and wherein said timer is configured to generate said make-break detection period in coordination with multiple refractory periods.

4. An implantable heart stimulating device as claimed in claim 1 comprising heart stimulating circuitry that operates with an escape interval, and wherein said timer is configured to generate said make-break detection period with a programmable length that is a percentage between 20% and 100% of a length of said escape interval.

5. An implantable heart stimulating device as claimed in claim 1 wherein said ECG sensing unit identifies a beginning of each heart cycle of said heart, and wherein ECG sensing unit resets said counter after each heart cycle.

6. An implantable heart stimulating device as claimed in claim 1 comprising an analysis unit that analyzes the ECG signal stored in said storage unit to identify specific defects or damages of said electrode lead or interaction of said electrode with the heart of the patient.

7. An implantable heart stimulating device as claimed in claim 6 comprising an alarm generator that emits a humanly perceptible alarm if said analysis unit identifies a defect or damage associated with said electrode lead or said electrode.

8. An implantable heart stimulating device as claimed in claim 1 wherein said non-temporal threshold is a threshold range for said magnitude of said cardiac potential signal, said threshold range having an upper magnitude boundary and a lower magnitude boundary.

9. A medical system comprising:
an implantable heart stimulating device comprising an electrode lead configured for in vivo implantation in a patient, said electrode lead carrying at least one sensing electrode configured to interact with the heart of the patient, as part of a complete current path, when the electrode lead is implanted in the patient, an ECG sensing unit that receives cardiac potential signals from said electrode, said ECG sensing unit being provided with a non-temporal make-break threshold indicative of a magnitude of said cardiac potential signal associated with an absence of successive making and breaking of said current path, said ECG sensing unit being configured to emit an output signal at a first output of said ECG sensing unit whenever said cardiac potential signal exceeds said threshold, a timer that generates a make-break detection period, a counter connected to said first output of said ECG sensing unit that generates a count representing a number of times that said cardiac potential signals exceeds said make-break threshold, and a storage unit connected to said counter and to a second output of said ECG sensing unit, said counter being configured to cause transfer of the cardiac potential signal obtained during said make-break detection period from said second output of said ECG sensing unit to said storage unit if said count in said make-break detection period exceeds a predetermined value;
an extracorporeal programming device;
communication units respectively contained in said implantable heart stimulating device and said programming device allowing said programming device to access the cardiac potential signal stored in said storage unit; and
said programming unit comprising an analysis unit configured to analyze the cardiac potential signal stored in said storage unit and communicated to said programming device to identify, based on a characteristic of the stored and communicated cardiac potential signal, a defect or damage of said electrode lead or interaction of said electrode with said heart.

10. A medical system as claimed in claim 9 wherein said non-temporal threshold is a threshold range for said magnitude of said cardiac potential signal, said threshold range having an upper magnitude boundary and a lower magnitude boundary.

* * * * *